US00PP25094P2

(12) United States Plant Patent
Friday

(10) Patent No.: US PP25,094 P2
(45) Date of Patent: Nov. 25, 2014

(54) PEACH TREE NAMED 'P.F. PARAMOUNT 24'

(50) Latin Name: *Prunus persica*
Varietal Denomination: P.F. Paramount 24

(71) Applicant: Paul Jan Friday, Coloma, MI (US)

(72) Inventor: Paul Jan Friday, Coloma, MI (US)

( * ) Notice: Subject to any disclaimer, the term of this patent is extended or adjusted under 35 U.S.C. 154(b) by 34 days.

(21) Appl. No.: 13/573,995

(22) Filed: Oct. 19, 2012

(51) Int. Cl.
*A01H 5/00* (2006.01)

(52) U.S. Cl.
USPC ..... Plt./198

(58) Field of Classification Search
USPC ..... Plt./198
See application file for complete search history.

*Primary Examiner* — Anne Grunberg
(74) *Attorney, Agent, or Firm* — Paul Friday

(57) ABSTRACT

A new and distinct variety of peach, *Prunus persica*, tree having the following unique combination of desirable features.

1. The new and distinct variety of peach tree is of spreading growth being a regular and productive bearer of large peaches having an average diameter above 2-¾".
2. Producing a very firm fruit having a resilient flesh texture.
3. Blossoms are non-showy when in full bloom.
4. A substantially spherical fruit with skin of dark red color overlying yellow at maturity
5. An mid-season maturing fruit of good taste, and freestone.

2 Drawing Sheets

Botanical classification: *Prunus persica.*

ORIGIN OF VARIETY

The new peach tree {hereinafter referred to as the 'P.F. Paramount 24'} was originated by Paul Friday in the experiment orchard, which is maintained for the purposes of breeding peach trees, located in Coloma, Mich. Coloma is located in the southwest section of Michigan, USDA Hardiness Zone 6A, with observed temperature ranges of minus 12 degree Fahrenheit to 90 degree Fahrenheit, also with annual rainfall of about 40 inches.

In an ongoing mass selection, breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for there adaptability to local and regional growing conditions. Seeds resulting from open pollination of the trees in the experimental orchard are regularly planted in mass to produce new populations of seedlings, which are cultured and monitored to maturity. Trees with superior attributes are retained for further observation and testing, and contribute seeds to advancing generations of new populations of seedlings.

The tree of this application, 'P.F. Paramount 24', was a single plant from one such a seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in an experimental orchard located in Coloma, Mich. The asexual propagation demonstrates that such reproduction of the characteristics of the tree are consistent and are established and transmitted through succeeding propagation.

SUMMARY OF THE VARIETY

The new and very distinct variety of peach tree is of moderate spreading growth and a regular and productive bearer of peaches. The 'P.F. Paramount 24' peach tree bears a very freestone peach of a diameter of 2¾" and up. The blossoms are characterized by being contracted or partially spread to approximately ¾-inch when in full bloom. At the same time petals of the blossoms are of lesser length than the length of petals of normal showy blossom as exemplified by the "Loring" (non-patented) peach blossom.

The blossoms of the present peach tree at full bloom may be characterized as being non-showy.

The leaves are above average in size. The limbs have notably short internodes.

The fruit at maturity is large, having flesh that is firm and is a yellow with red around pit cavity.

The skin is smooth having exceptionally little down and is of dark red color overlying dark yellow. At maturity the peach is spherical having an average diameter ranging between about 2-¾" to 3".

The stone is notably an elongated seed with the base unusually located off center.

The fruit has a firm flesh and may be described as resilient to the extent that the flesh is yieldable and restorable to its original state when subjected to impact forces, which may cause permanent deformities in peaches of commercial varieties. The firmness of the fruit facilitates handling and packaging of the peaches without damaging the same for shipment. This results in less spoilage and also increases the shelf life.

The fruit matures in the mid-part of the peach growing season in southwestern Michigan. The fruit as mentioned heretofore is of dark red color overlying dark yellow and has a very attractive appearance.

The variety is self fertile.

BRIEF DESCRIPTION OF THE PHOTOGRAPHS

In the accompanying drawings page one, the top photograph shows the leaves of the plant, depicting upper and lower sides. A tape measure is included showing the length of a leaf.

The bottom photograph shows two (2) whole fruits with one bisected across the axis showing the extent of the clear yellow flesh with red streaks projecting from the red around the pit. A tape measure is included to show the good size of this fruit.

Page two shows the base off center.

DESCRIPTION OF VARIETY

The detailed botanical description of the foliage and fruit of the new variety of peach tree is based upon observations of the specimens grown at Coloma, Mich. with the color terminology, other than the terminology expressed in common terms, in accordance with the Pantone Matching System {PMS} as used internationally to identify printed colors.

Botanical classification: *Prunus persica* cultivar 'P.F. Paramount 24'.

Tree:

*Age*.—Twelve (12) years.
*Height*.—Unpruned 8.5'.
*Width*.—Unpruned 7.5'.
*Size*.—Medium.
*Vigor*.—Moderate.
*Density*.—Medium.
*Form*.—Spreading.
*Production*.—Good.
*Bearer*.—Regular.
*Disease resistance to bacterial leaf and fruit spot*.—Very resistant.
*Rootstock*.—Grown in its own roots.

Trunk:

*Bark*.—Gray (450).
*Size*.—Medium.
*Surface*.—Rough.
*Diameter*.—3.5" diameter — 18" above ground at 4 years of age.
*Lenticels*.—Pronounced.
*Lenticels color*.—Panton # 400.
*Lenticels size*.—⅛".

Branches:

*Size*.—Medium 2-½" diameter 6" from trunk.
*Surface*.—Semi-smooth.
*Lenticels per square inch*.—Ten (10).
*Lenticels color*.—Pantone # 131.
*Lenticels size*.—⅛" (more prominent to underside of branch).
*Crotch angles*.—45 degrees angles.
*Branch color*.—Dark Gray (403).
*Internode length*.—¾ inch.

Leaves:

*Size*.—Average length 7-¼" average width 1-½".
*Form*.—Lanceolate — pointed.
*Thickness*.—Medium.
*Texture*.—Glabrous.
*Margin*.—Serrated.
*Leaf base shape*.—Acute.
*Leaf apex shape*.—Pointed.
*Petiole length*.—⅜".
*Gland*.—2-4 on either side of the petiole.
*Gland shape*.—Oval.
*Gland color*.—Brown.
*Leaf color*.—Adaxial (Top) or upper leaf surface — green (350).
*Leaf color*.—Abaxial (Bottom) or bottom leaf surface — green (384).

Flower buds:

*Size*.—¼" long — ⅝" wide.
*Bud shape*.—Ovate.
*Bud color*.—Pantone # 243.

Flowers:

*Blooming period*.—Early May in Southwest Michigan.
*Bloom size*.—¾" diameter.
*Bloom depth*.—⅜" deep.
*Size of petals*.—½" long — ¼" wide.
*Shape of petals*.—Cupped.
*Petal margins*.—Entire (smooth).
*Petal base shape*.—Pointed.
*Petal apex shape*.—Ovate.
*Petal color*.—Pantone # 217.
*Number of petals*.—Five (5).
*Sepal size*.—¼" long — ⅛" wide.
*Sepal shape*.—Flat.
*Sepal apex*.—Pointed.
*Sepal base*.—Flat.
*Sepal color*.—Pantone # 216.
*Number of sepals*.—Five (5).
*Number of anthers*.—20.
*Anther color*.—Pantone # 132.
*Number of stamens*.—20.
*Stamen length*.—⅜".
*Stamen color*.—Pantone # 232.
*Pistil length*.—⅜".
*Pistil color*.—Pantone # 113.
*Pollen*.—Present.
*Flower color*.—Pink (Pantone # 217).
*Number flowers per cluster*.—2.
*Fragrance*.—Very slight fragrance.

Fruit:

*Maturity when described*.—Firm ripe.
*Date of first picking*.—August 24$^{th}$ in Southwestern Michigan.
*Date of last picking*.—August 30$^{th}$ in Southwestern Michigan.
*Size*.—Average 2-¾".
*Form*.—Spherical.
*Suture*.—Not Pronounced — stays firm.
*Weight*.—7.5 oz.

Skin:

*Thickness*.—Medium as compared to the species.
*Texture*.—Medium as compared to the species.
*Tendency to crack*.—None.
*Down*.—Light (short as compared to the species).
*Color*.—About 80% red (Pantone # 202) over dark yellow (Pantone # 143).

Flesh:

*Texture*.—Firm, non-melting free of fiber.
*Ripens*.—Evenly.
*Flavor*.—Very good.
*Aroma*.—Pleasant, excellent.
*Eating quality*.—Excellent.

*Brix*.—Average of 12%.
*Color*.—Yellow Pantone # 113.
*Pit cavity color*.—Red around cavity Pantone # 193.

Stone:
*Type*.—Freestone.
*Size*.—1¾" Long 1¼" Wide ⅝" Thick.
*Form*.—Oblong.
*Base*.—Flat ⅛", off center.
*Apex*.—Pointed.
*Sides*.—Even.
*Surface*.—Furrowed.
*Color*.—Brown Pantone # 174.
*Tendency to crack*.—None.
*Kernel*.—¾" Long ½" Wide 1/16" Thick.
*Kernel taste*.—Bland.

Use: Dessert.
Shipping quality: Very good.
Keeping quality: Very good (up to three (3) weeks).
Disease resistance: The fruit is resistance to brown rot.
Chilling hours: 750 hours.

The tree and its fruit herein described may vary slight as a result of differences in climatic or soil conditions or cultural practices under which the tree may be grown. It is to be understood that the description of the new variety as set forth herein is that of the tree grown under the ecological conditions prevailing at Coloma, Mich.

COMPARISON OF VARIETY

'P.F. Paramount 24' variety ripens in the same time frame as the variety 'P.F. 24-007' (U.S. Plant Pat. No. 9,895). Both of them were developed in my breeding program.

Comparing the 'P.F. Paramount 24' variety with the 'P.F. 24-007' patented variety, following notable genetic differences are present.

'P.F. 24-007' has vigorous upright growth whereas 'P.F. Paramount 24' has moderate spreading growth. The 'P.F. 24-007' has a stone that is 1½ inches long, 1 inch wide, and ¾ inch thick. The stone of 'P.F. Paramount 24' is longer, wider and thinner with dimensions of 1¾ inch long, 1¼ inch wide and ⅝ inch thick. The bloom of 'P.F. 24-007' is larger than 'P.F. Paramount 24' bloom, 'P.F. 24-007' 1¼ diameter at full bloom, whereas 'P.F. Paramount 24' flower is ¾ diameter when fully open. The skin color of 'P.F. 24-007' is lavender red overlaying a light to whitish yellow color at maturity. 'P.F. Paramount 24' has skin of dark red color overlaying dark yellow color.

Comparing 'P.F. Paramount 24' with another mid season peach from my breeding program, 'P.F. 22-007' U.S. Plant Pat. No. 16,663, Jun. 20, 1006:

'P.F. Paramount 24' has a bloom ¾ in diameter at full bloom whereas the 'P.F. 22-007' variety has a bloom that is a full inch when in full bloom. The base of the stone in the fruit of 'P.F. Paramount 24' is notable located off center. The base of the 'P.F. 22-007' is straight. 'P.F. Paramount 24' leaves have an average length of 7¼" and the 'P.F. 24-007' variety has a leaf that average is 5½" in length.

What is claimed is:

1. A new and distinct variety of peach tree substantially as herein illustrated and described.

* * * * *

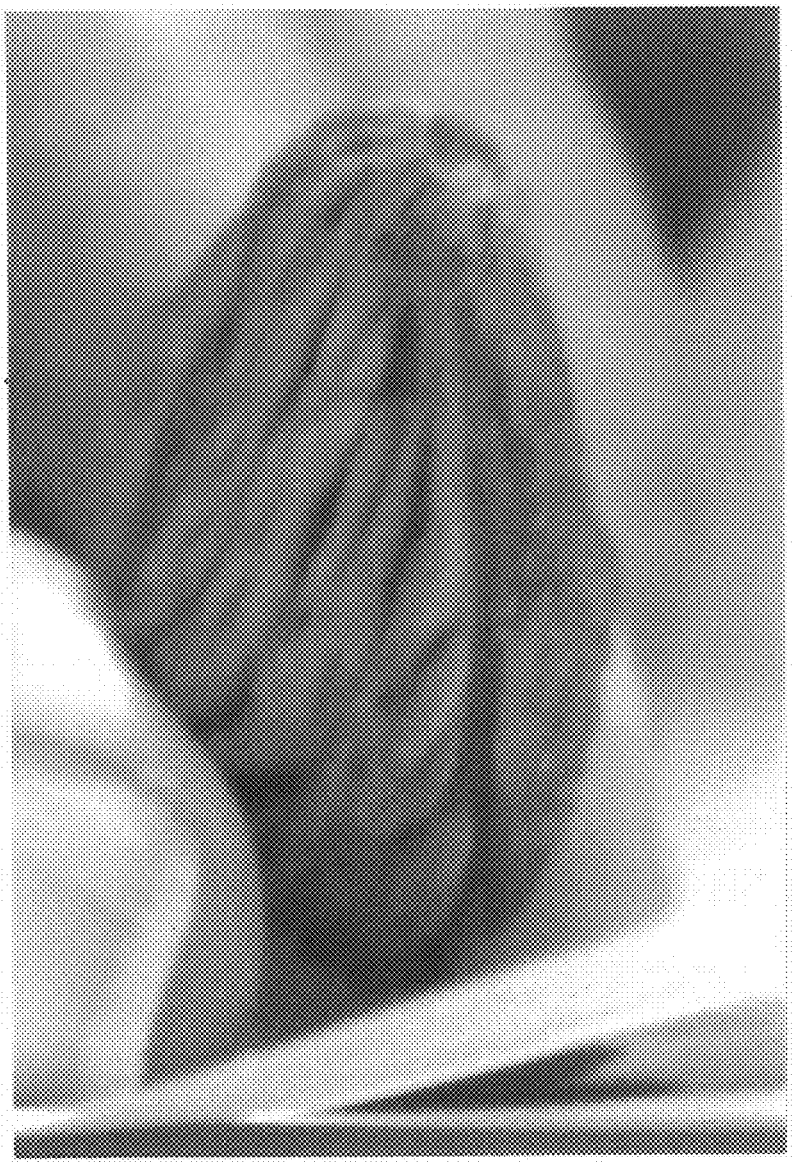

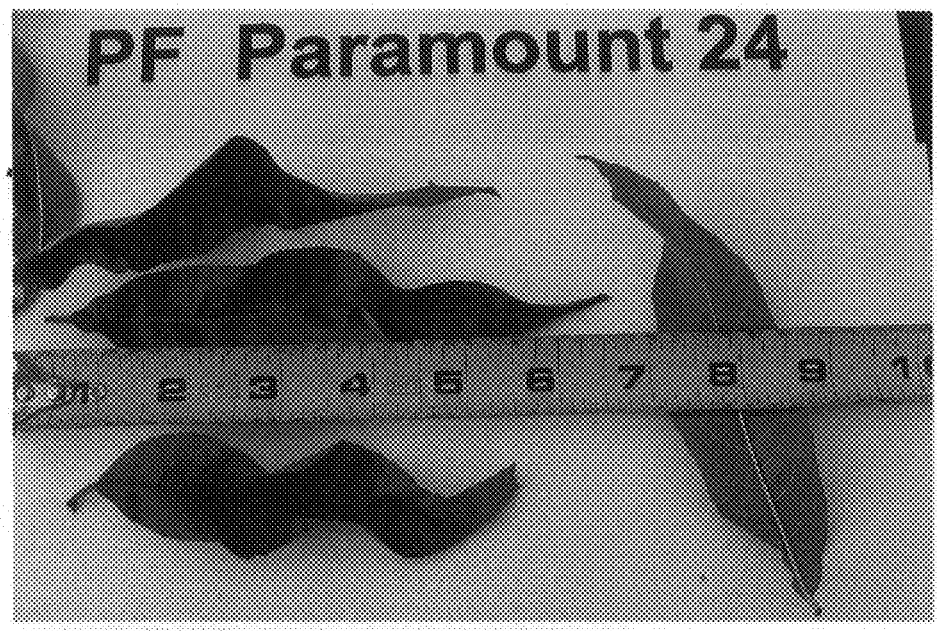
PF Paramount 24
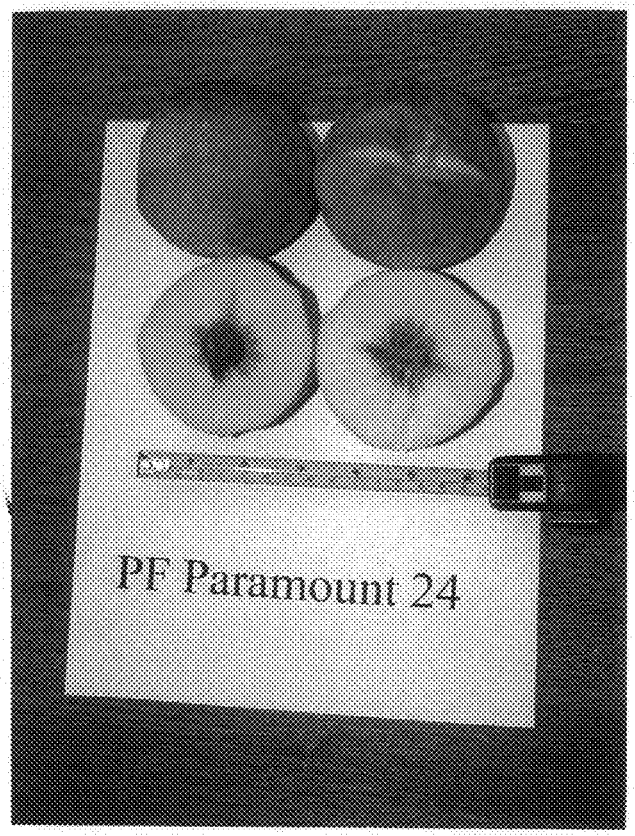
PF Paramount 24